(12) United States Patent
van Ooyen et al.

(10) Patent No.: US 8,862,266 B2
(45) Date of Patent: Oct. 14, 2014

(54) AUTOMATED DISPENSARY APPARATUS FOR DISPENSING PILLS

(75) Inventors: Wes van Ooyen, Burlington (CA); Todd Willick, Mississauga (CA); Derek Bessette, Milton (CA); Richard Panetta, Milton (CA)

(73) Assignee: MedAvail, Inc., San Francisco, CA (US)

( * ) Notice: Subject to any disclaimer, the term of this patent is extended or adjusted under 35 U.S.C. 154(b) by 978 days.

(21) Appl. No.: 12/611,089

(22) Filed: Nov. 2, 2009

(65) Prior Publication Data

US 2010/0264158 A1    Oct. 21, 2010

Related U.S. Application Data

(60) Provisional application No. 61/170,642, filed on Apr. 19, 2009.

(51) Int. Cl.
| | | |
|---|---|---|
| *G06F 17/00* | (2006.01) | |
| *G07F 17/00* | (2006.01) | |
| *G07F 11/44* | (2006.01) | |
| *A61J 7/00* | (2006.01) | |

(52) U.S. Cl.
   CPC .......... *G07F 11/44* (2013.01); *G07F 17/0092* (2013.01); *A61J 7/0084* (2013.01)
   USPC ........... 700/240; 221/277; 221/241; 221/261

(58) Field of Classification Search
   USPC ........... 700/236, 240; 221/224, 241, 261, 277
   See application file for complete search history.

(56) References Cited

U.S. PATENT DOCUMENTS

| | | | | |
|---|---|---|---|---|
| 5,752,368 | A * | 5/1998 | Tobe | 700/244 |
| 6,085,938 | A * | 7/2000 | Coughlin | 221/203 |
| 6,161,721 | A * | 12/2000 | Kudera et al. | 221/9 |
| 7,562,791 | B2 * | 7/2009 | Yuyama et al. | 221/265 |
| 7,886,931 | B2 * | 2/2011 | Handfield et al. | 221/154 |

* cited by examiner

*Primary Examiner* — Timothy Waggoner
(74) *Attorney, Agent, or Firm* — DeSandro Law Group PLLC; Bradley K. DeSandro

(57) ABSTRACT

A pill dispensing apparatus has a pill delivery station, a pill receiving station, and a pill singulator. The singulator receives and supports pills delivered from the delivery station and is spun to drive pills supported on the tray around the tray axis. A wiper guide guides the driven pills towards the pill receiving station and at the same time singulates the pills by establish spacing between them. The singulated pills are then deflected to a pill drop zone where they drop into a container.

21 Claims, 10 Drawing Sheets

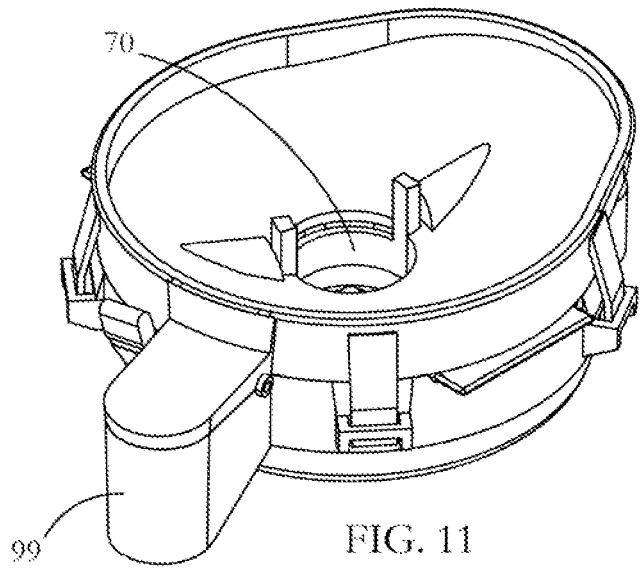
FIG. 11
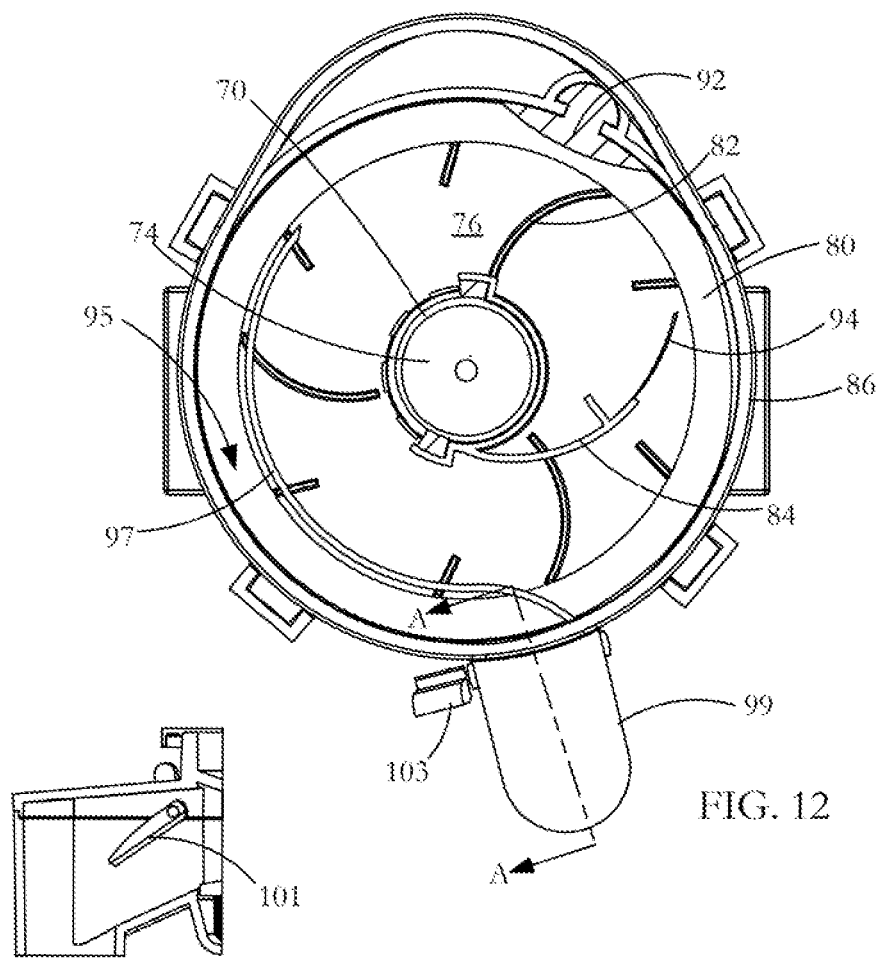
FIG. 12
FIG. 13

AUTOMATED DISPENSARY APPARATUS FOR DISPENSING PILLS

CROSS REFERENCE TO RELATED PATENTS

This patent application is claiming priority under 35 U.S.C. §119to a provisionally filed patent application entitled Automated Dispensary Apparatus for Dispensing Medicaments, having a provisional filing date of Apr. 19, 2009, and a provisional Ser. No. of 61/170,642.

FIELD OF THE INVENTION

The present invention relates to a method and apparatus for dispensing pills from a bulk store of pills and has particular application for a medicament dispensary kiosk.

DESCRIPTION OF RELATED ART

In this specification, the term "medicament" encompasses drugs and any and all other materials dispensed subject to presentation of a prescription, and the term "pill" encompasses pills, capsules, lozenges and like discrete items intended for ingestion.

The traditional means of dispensing prescribed medicaments involves a doctor meeting with a patient and prescribing a medicament based on a particular diagnosis, and then hand writing and signing a prescription for the patient to carry to a pharmacist at a pharmacy location for fulfillment. In recent years, two significant advances have occurred in the field of medicament dispensing. The first is the advent of electronic prescription capturing methods, systems and apparatus, which improve the overall accuracy and patient record-keeping associated with prescribing drugs. The second is the advent of automated apparatus, typically configured as kiosks, from which medicaments can be automatically dispensed, the kiosks being located for convenient patient access, such as at a doctor's premises, a hospital or mall, and being networked with a system server for inventory control and management. In this regard, reference may be made to applicant's copending PCT application Ser. No. PCT/CA2007/001220 related to a method, system and apparatus for dispensing drugs.

More specifically, the PCT application describes a networked system having a server, a database of patient information linked to the server, a first client having input means linked to the server and operable to generate a script for a medicament prescribed to a user, and a second client comprising an automated apparatus for dispensing medicaments (referred to in said PCT application as a robotic prescription dispensary) operable to recognize a human and/or machine readable description in the script, and to provide validating cross-referencing between the description and patient information as a prelude to dispensing a drug to the user on the basis of the input script. A doctor in a clinic can be a third client having input means linked to the server to input appropriate prescription information, or accept certain prescription information from the database as being applicable in the particular case for a particular patient. Further, the doctor's client device can be operable to display patient information, e.g., drug history, insurance coverage, etc., and a printer module can print the script as a paper print-out.

The server and database enable storing, compiling and retrieval of patient data including name, address, and diagnostic and drug history. Access to the database can be provided to both the doctor and the automated apparatus for dispensing medicaments via the server, via a secure connection, or via a link between the system and a clinic's existing clinic management system or patient database.

The system described in PCT/CA2007/001220 has a user interface for receiving input data from the user and for guiding the user through a medicament dispensing procedure. The system also has a teleconferencing or video-conferencing means enabling communication between the user and a human validation agent, such as a licensed pharmacist, who may be connected into the system from a remote location. The user interface also includes a scanning means for capturing an image of the script for validation by the validation agent.

An authentication means for confirming the identity of the user may, for example, prompt the user for a personal identification number, to provide biometric identifying data, or to provide answers to questions that will identify the user when cross-referenced with patient information stored on the networked database. Once the user is recognized, the dispensary apparatus prompts the user for a script and the apparatus processes the user-input script either by the above-mentioned human validation agent or by processing the machine readable description, which may be a bar code. This information can be verified with the server and the database. The apparatus may also interface with the server for the adjudication of insurance claims and for determining amounts to be paid by patients. The patient either accepts or rejects the transaction. If the transaction is accepted, the apparatus interfaces with the server in effecting a payment transaction, for example, by prompting the patient for credit card information. Prescription labels and receipts are printed. The apparatus confirms that the drug is correct and delivers it to a dispensing area for retrieval by the user while retaining the script in a lock box, and verifying that the purchased drug product has been retrieved. Further, the apparatus may print and/or provide to the user educational materials relevant to the medicaments that have been dispensed. The medicament dispensary kiosk may be located in a doctor's office or clinic. The interaction between a user and the user interface coupled with access to the various networked functionalities means that a patient can obtain prescribed medicaments without having to attend a pharmacy or drug store.

SUMMARY OF THE INVENTION

According to one aspect of the invention, there is provided a pill dispenser comprising a pill delivery station, a pill receiving station, and a pill singulator for singulating pills, the singulator including a tray for supporting pills delivered from the delivery station, a drive to spin the tray about an axis to drive pills supported on the tray in a spin direction, and a guide to guide the driven pills towards the pill receiving station and to establish spacing between the driven pills.

The pill delivery station may included a pill hopper and a delivery chute intermediate the hopper and the tray, with the chute position relative to the tray being adjustable to tailor a spacing between the chute and the tray to the size of pills to be delivered and singulated. The delivery of pills into the tray is further regulated by the rate of spin of the tray which draws pills supported by the tray away from the delivery chute. The guide is suitably a wiper guide mounted close to a drive surface of the tray, the wiper guide shaped and positioned to guide pills delivered to a hub region of the tray and driven by the spinnning tray away from the hub region. The wiper guide is preferably arcuate in form so as to effect pill singulation by causing a space to open up between successive pills as they are driven by the tray spin against and along the arcuate guide.

The tray is preferably formed as a shallow conical disc with said spacing between the delivery chute and the tray established at a raised hub region of the disc shaped tray and with the wiper guide shaped and positioned to guide the driven pills from the hub region of the tray to a boundary region of the tray where singulated pills are confined by a boundary wall. The tray can have a gutter region adjacent the boundary wall sloping downwardly towards the wall, whereby pills approaching the outside edge of the tray fall and lodge against the wall. The upper surface can be formed so as to drive the pills as by having a high coefficient of friction and/or by having upstanding projections.

The pill dispenser can include a restricting mechanism near the boundary wall to discourage further drive of the pills in the spin direction other than as singulated pills. The restricting mechanism may include a spring member mounted at an outer end of the wiper guide to intercept any pills that are unsingulated and are being conveyed by the tray as a lumped aggregation of pills. The spring member is spaced from the boundary wall so as to present the pills a funnel aperture large enough to permit passage of single pills in a range of sizes. The spring member tends to break up a lumped aggregation of pills to produce a sequence of singulated pills. The spring member is made to deform elastically from its mounting orientation to avoid jamming by such a lumped aggregation.

The restricting mechanism may further include an attachment which can be mounted to the boundary wall so as to have part thereof projecting radially inwardly from the wall into the path of the circulating pills. The attachment can be any of a range of possible sized tailored to the particular size and shape of pills to be dispensed. The projecting part intercepts and deflects from the gutter region pills that are larger than the particular size.

Preferably, the pill dispenser includes closures to prevent ingress of contaminants to any part of the pill dispenser where pills may be present, the dispenser further including seals at the junctions of the closures and other parts of the dispenser to prevent passage of dust or vapourous contaminants. The pill dispenser may further include internal seals to prevent internally generated contaminants from reaching the pills, such internal contaminants originating, for example, from certain of the dispenser module's moving parts.

The dispenser may further comprise a gate movable from a closed to an open position to permit singulated pills to enter a pill fall zone within which a container, such as a pill bottle, is positioned to collect falling pills and where a sensing mechanism detects and counts the pills falling in the fall zone to enable the supply of pills from the hopper to be halted when a required number of pills have passed into the fall zone.

The dispenser may further comprise a container sub-system for picking a container, such as a bottle, from a store thereof and for transferring the picked container to the pill fall zone to receive pills. The pill dispenser may further comprise a capping sub-system to which a container filled with pills is brought, the capping sub-system including a store of caps, a transfer mechanism to transfer a cap from the cap store to the filled bottle, and a mechanism to snap lock or screw the transferred cap onto the container.

According to another aspect of the invention, there is provided a method of dispensing pills comprising delivering pills from a hopper to a singulating zone, delivering pills from the singulating zone to a receiving station, and at the singulating zone, supporting the pills delivered from the hopper on a tray, spinning the tray to drive the supported pills in a drive direction, guiding the driven pills towards the pill receiving station, and singulating the driven, guided pills by establishing a spacing between successive pills.

BRIEF DESCRIPTION OF THE DRAWINGS

For simplicity and clarity of illustration, elements illustrated in the following figures are not drawn to a common scale. For example, the dimensions of some of the elements are exaggerated relative to other elements for clarity. Advantages, features and characteristics of the present invention, as well as methods, operation and functions of related elements of structure, and the combinations of parts and economies of manufacture, will become apparent upon consideration of the following description and claims with reference to the accompanying drawings, all of which form a part of the specification, wherein like reference numerals designate corresponding parts in the various figures, and wherein:

FIG. 11 is perspective view of a pill dispensing module according to another embodiment of the invention, the module shown with a hopper lid removed;

FIG. 12 is a view from above of the module of FIG. 11 with a hopper lid and hopper element removed;

FIG. 13 is a scrap sectional view on the line A-A of FIG. 12;

DETAILED DESCRIPTION OF THE INVENTION INCLUDING THE PRESENTLY PREFERRED EMBODIMENTS

In our copending patent application PCT/CA2009/001186, we describe a particular medicament dispensary apparatus for delivering medicaments to users, the apparatus having a drug vault with a pre-packaged product storage container for containing inventory pre-packaged medicament product and a bulk product storage container for containing inventory medicament in bulk form. The apparatus has a control system operable to dispense bulk form inventory medicament from the bulk product storage container, to package the medicament as a suitable package, and to pick and deliver the package to a delivery zone. One form of bulk products is pills. In a medicament dispensary kiosk of the type contemplated, an efficient method and apparatus for dispensing pills is required.

Figure 1:
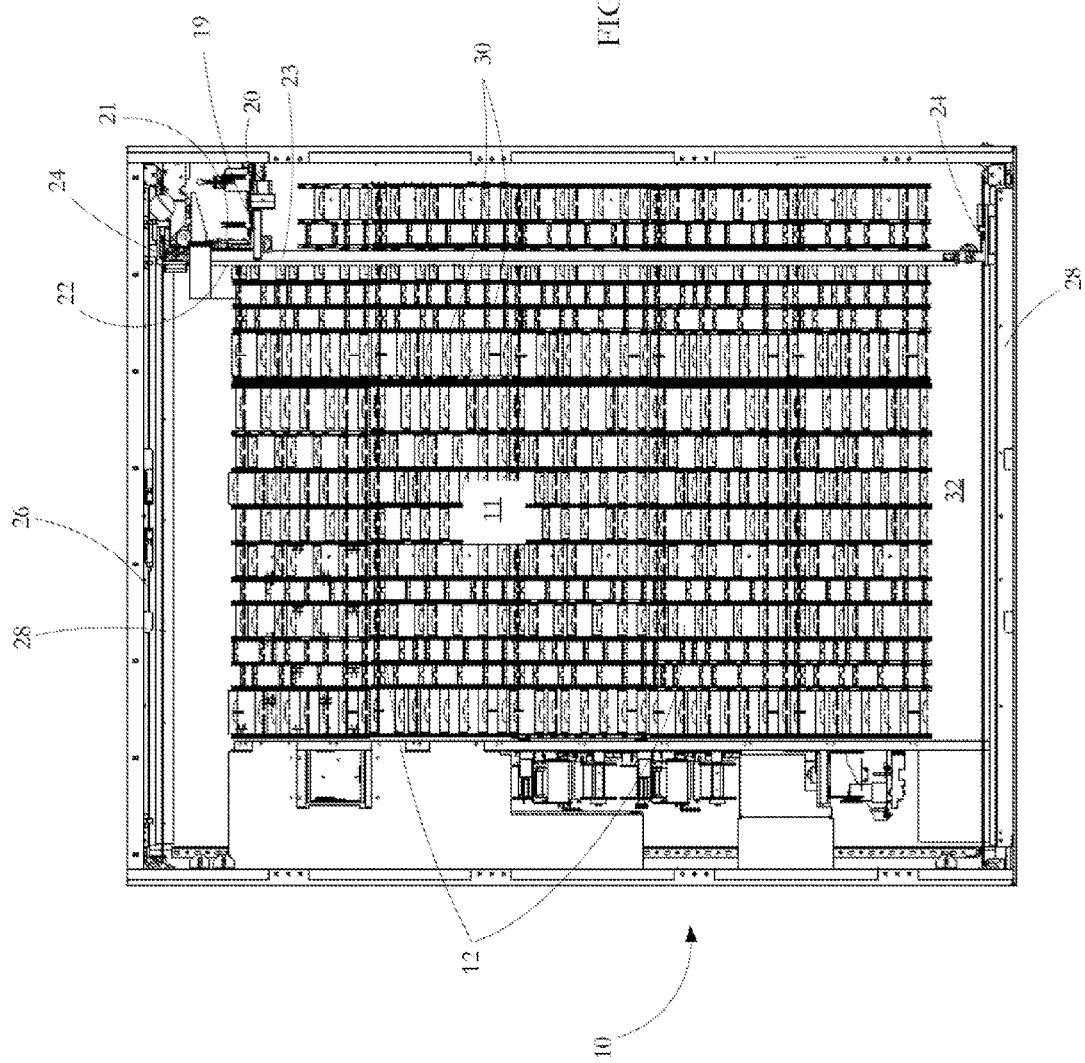
FIG. 1 is a front view of a storage apparatus for a package dispensing kiosk.

Referring in detail to FIG. 1, there is shown a front view of a cabinet 10 for a dispensing kiosk, the cabinet having a rack 11 of storage bins 12 arranged in a row and column array. The bins vary in shape and size to accommodate different sizes of packages to be dispensed. Particularly for the application envisioned for the present invention, the rack of storage bins is formed as a secure back-end medicament storage vault. The storage vault is, in use, combined with a front-end unit (not shown) which bars unauthorized access to the drug vault, but which can be opened to expose the drug vault for servicing. Mounted in the front end unit is an interface unit (not shown) at which a user, can enter data, communicate with a remote expertise or data records through a data or teleconference link, and collect dispensed packages, etc.

As shown in FIG. 1, a pick head 20 is mounted on a platform 19 which is itself mounted on a vertically reciprocable carriage 21 driven by a belt drive 22 along a vertical guide rail 23. The rail 23 is mounted between two linked, horizontally reciprocable carriages 24. The carriages 24 are driven by a belt drive 26 along horizontal rails 28. The carriages 21 and 24 are movable in a plane which extends parallel to a front access side of the bin rack 11. By appropriate movement of the carriages, the pick head 20 can be driven under the control of a control system in X and Y directions to any selected position within the full vertical and horizontal extent of the medicament vault. The pick head has a platen which is reciprocal in the Z direction to pick or place a transported item relative to a storage bin 12. The pick head 20 is used to pick a chosen package from its position in the rack of bins and, if part of a stack or row of packages, from its position within the stack or row, in preparation for dispensing the package at an access bay in the front end interface unit. Optionally, the pick head 20 can also be used to load medicament packages in a bin in a reverse process. Particular pick head mechanisms for use with the illustrated rack of the present invention are described in copending U.S. patent application Ser. No. 12/503,989 which is herein incorporated in its entirety by reference. The platform 19 supports other mechanisms for manipulating other elements involved in dispensing medicaments from a function zone as will be described presently.

Figure 2:
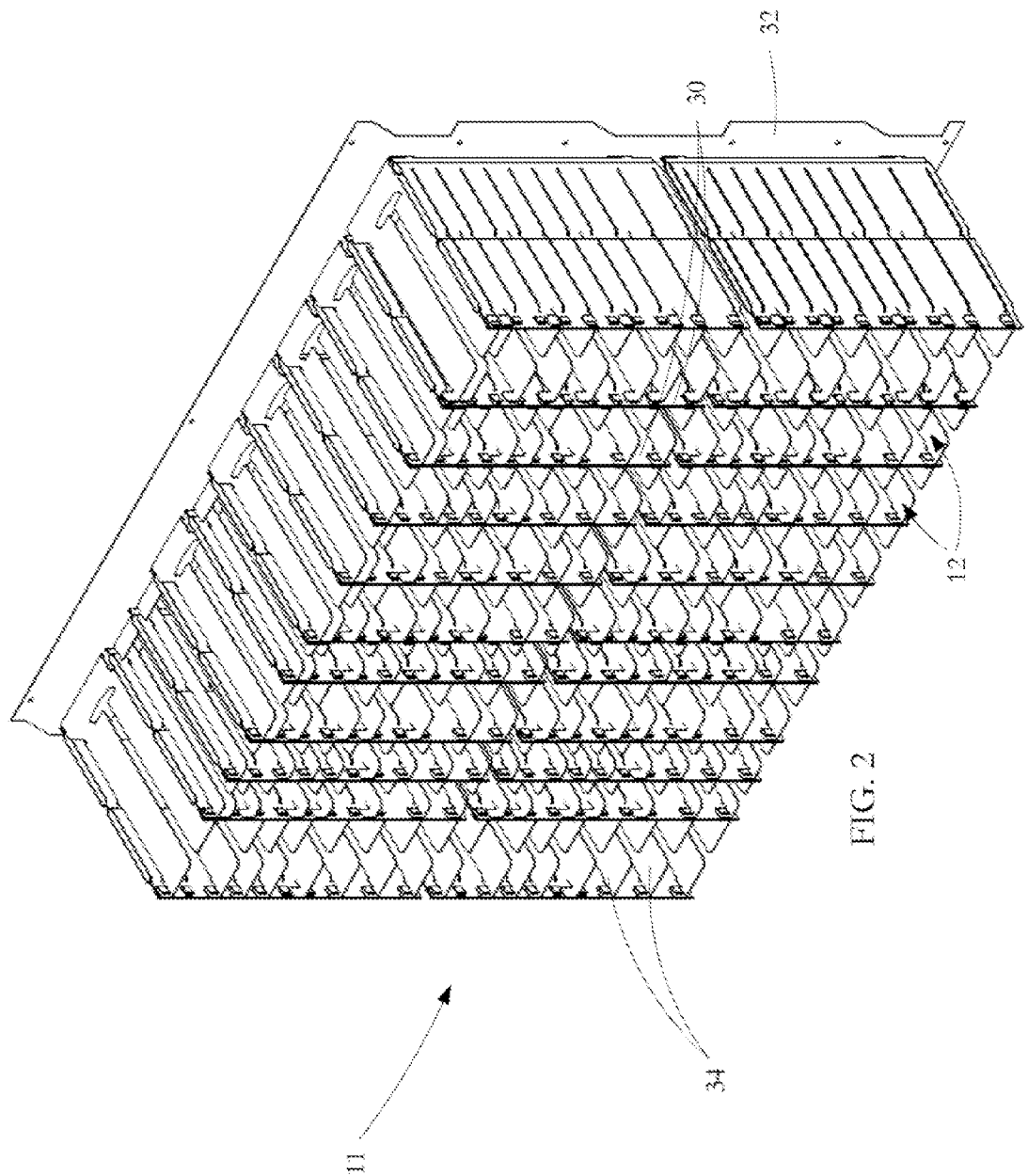
FIG. 2 is a perspective view of a bin rack forming part of the storage apparatus of FIG. 1.

As shown in FIGS. 1 and 2, the bins 12 occupy the total height and breadth of the rack. When assembled, vertical partition members 30 are mounted to a rack back panel 32 and horizontal floor members 34 are mounted to the vertical partition members 30 as described in copending U.S. patent application Ser. No. 12/541,307 which is herein incorporated in its entirety by reference. The spacings of adjacent vertical partition members 30 and of adjacent horizontal floor members 34 are adjustable. In this way, the bin sizes can be configured to offer a range of bin heights and bin widths with a view to tailoring bin size to a range of sizes of package or stacks/rows of packages to enable the package or packages to be stored in the bins 12 without undue wastage of storage volume.

Figure 3:
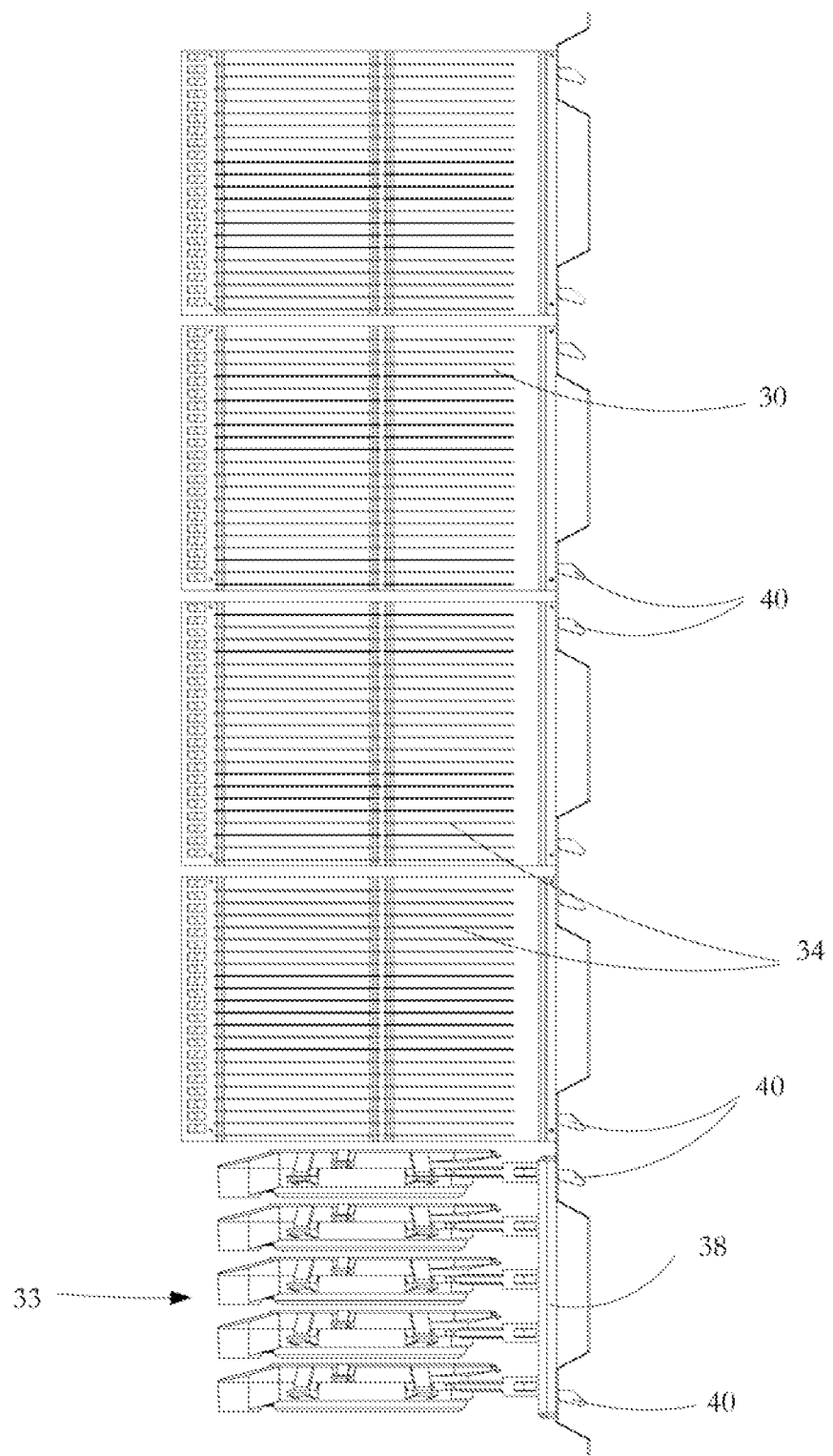
FIG. 3 is a side view of the storage apparatus of FIG. 1.
Figure 4:
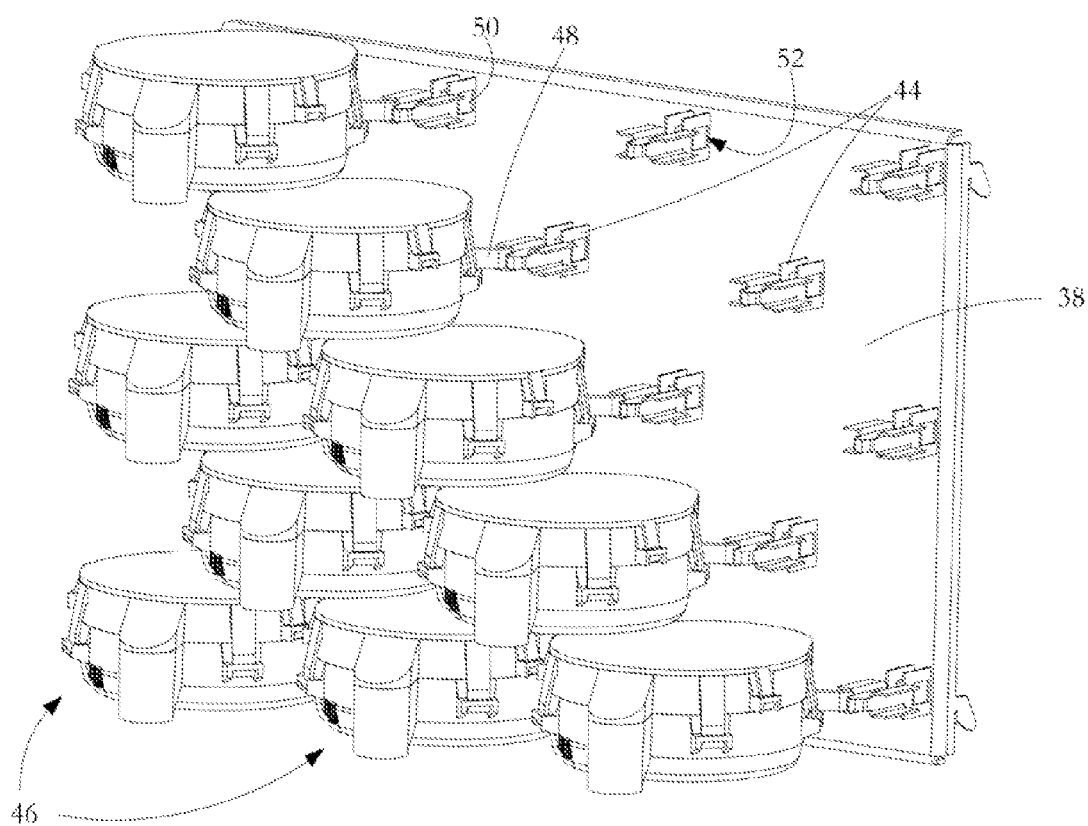
FIG. 4 is a perspective view of a sub-panel mountable on a rack system.

As shown in an alternative configuration in side view in FIG. 3, vertical partition members 30 defining such bins extend over only a part of the rack height with a function zone 33 of the cabinet housing a number of function modules which, in the embodiment illustrated, are pill dispensing modules 46. At the function zone, and mounted against the back panel 32, is a sub-panel 38. The sub-panel has tongues 40 which are inserted into corresponding slots in the back panel to fix the sub-panel 38 in place. As shown in perspective view in FIG. 4, an array of brackets 44 extend from a front face of the sub-panel and pill dispensing modules 46 are mounted on the brackets. The modules 46 have arms 48 formed to permit a predetermined range of spring flexure. At the end of each arm is a projection 50 which cooperates with a corresponding detent 52 on a respective bracket 44 to enable the pill dispensing module 46 to be clipped to and suspended in an operational position from the sub-panel 38.

One embodiment of pill dispensing module 46 is shown in detail in FIGS. 5 to 10. As shown in the plan view of FIG. 5, the module has a pill entry zone 53, a pill singulating zone 56 and a pill exit zone 60. In use, the module is operated to deliver a required number of pills 61 from a hopper 54 to a container (not shown) positioned at the exit zone for packaging and subsequent access by the platform 19.

The pill dispensing module is one of a number of function modules that can be mounted on the sub-panel 38. Another form of function module (not shown) has a bulk material storage element and is used to reconstitute, mix, and/or cause a reaction between, bulk materials for subsequent pick of a prepared medicament from the module. A further form of function module (not shown) comprises a dilution unit to dilute a medicament concentrate with water or other diluent at the time of medicament dispensing. The size of the function zone can be tailored to the particular type and number of functions to be performed by selecting a required size of sub-panel(s) 38 and mounting the required number and types of function modules to the or each sub-panel. In an alternative embodiment of function zone (not shown), some or all of the function modules are mounted directly to the back panel 32. Some or all of the storage bins 12 and/or function modules may be located in a zone of the bin rack which is at room temperature, while others may be located in a controlled temperature section such as a refrigerated zone for proper storage of medicaments that are prone to deterioration at room temperature.

Figure 5:
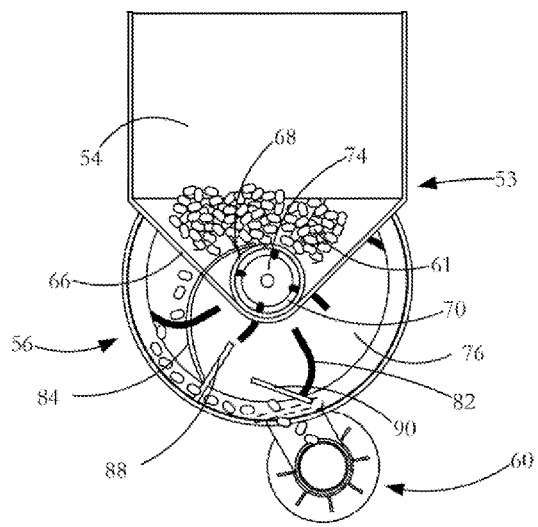
FIG. 5 is a view from above of a pill dispensing module according to one embodiment of the invention.
Figure 6:
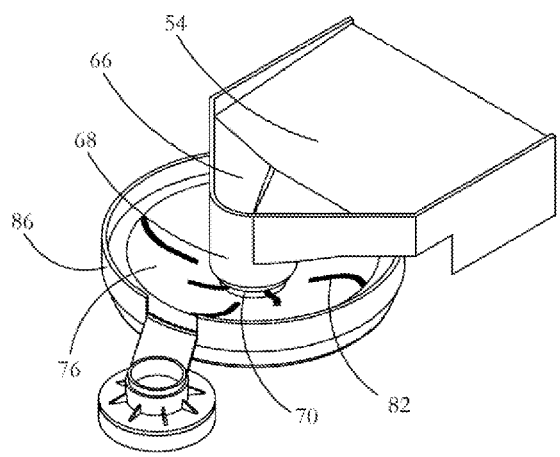
FIG. 6 is a perspective view of the module of FIG. 5.
Figure 7:
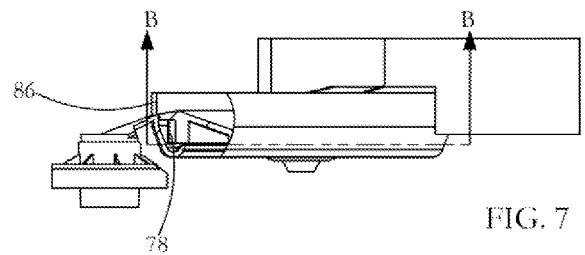
FIG. 7 is a side view of the module of FIG. 5.
Figure 8:
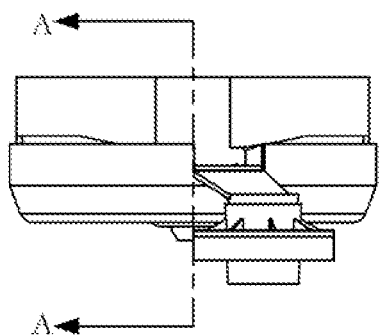
FIG. 8 is a front view of the module of FIG. 5.
Figure 9:
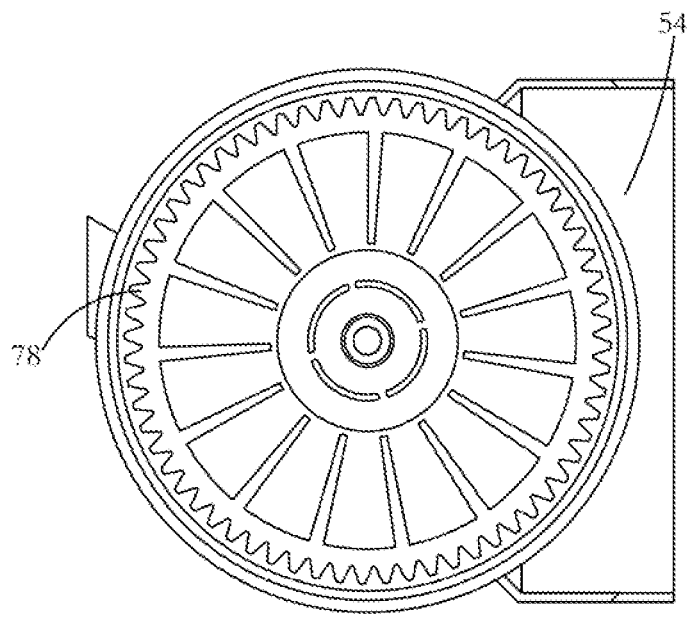
FIG. 9 is a view from below of the module of FIG. 5 taken on the line B-B of FIG. 7.
Figure 10:
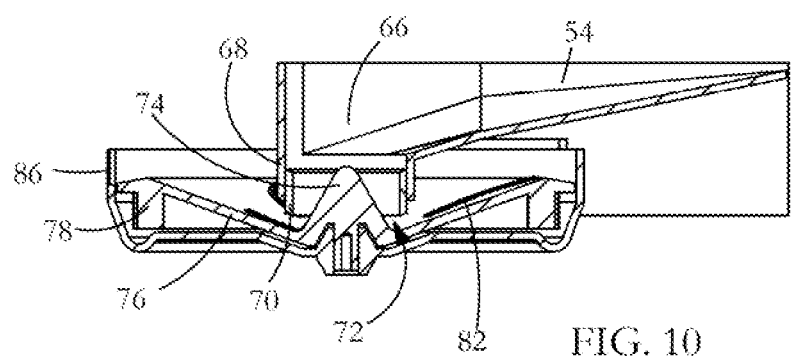
FIG. 10 is a view taken on the line A-A of FIG. 8.

The pills 61 to be dispensed from the module 46 may have any of a range of shapes and sizes. The module is formed of several layers which are clipped together. FIG. 5, which shows the module with lid removed, illustrates the hopper 54 and an exit funnel 66 with a vertically oriented, integrally formed cylindrical exit chute 68. Mounted within the exit chute is an annular cylindrical limiter 70. An outer surface of the limiter 70 screw engages an inner surface of the chute to enable the limiter to be screw adjusted vertically in the chute. At a lower layer of the module is a pill support tray 76. The width of an annular pill exit aperture 72 extending between the limiter 70 and a conical hub part 74 of the pill support tray can be adjusted to match the aperture size to the shape and size of pills to be dispensed.

Figure 14:
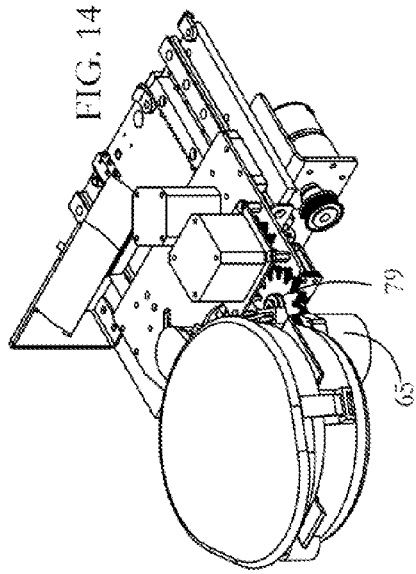
FIG. 14 is a perspective view of the module of FIG. 5 showing the module with lid in place and with the module being serviced by a drive mechanism.

A ring gear 78 on a lower surface of the tray 76 has teeth that mesh with a drive gear shown in FIG. 14 to spin the tray during the pill dispensing process. The tray 76 is generally disc shaped with an upper surface of the tray sloping downwardly towards the hub part 74 to define a dish form. The upper surface of the tray has a high friction coefficient, except at the hub part 74 and has an integrally formed series of low profile curved ridges 82.

As shown in FIG. 5, a wiper guide 84 is mounted above the tray 76 with its lower edge close to the tray upper surface so as to wipe the tray as the tray spins. The guide 84 has an arcuate form and extends from the hub region 74 almost to an outer edge of the tray. Mounted close to the tray upper surface and immediately adjacent a boundary wall 86 within which the tray spins is a separator 88. The separator has an aperture located and dimensioned to pass pills to the pill exit zone 60, one pill at a time. If pills arrive at the separator 88 as a group, all but one of the pills are stripped away, with the stripped pills either being respositioned in singulated fashion by agitation from the spinning tray or being rejected and returned to a pill store for later dispensing. The separator 88 is located downstream of the end of the wiper guide 84 in the tray spin direction and a gate 90 is located downstream of the separator.

Figure 15:
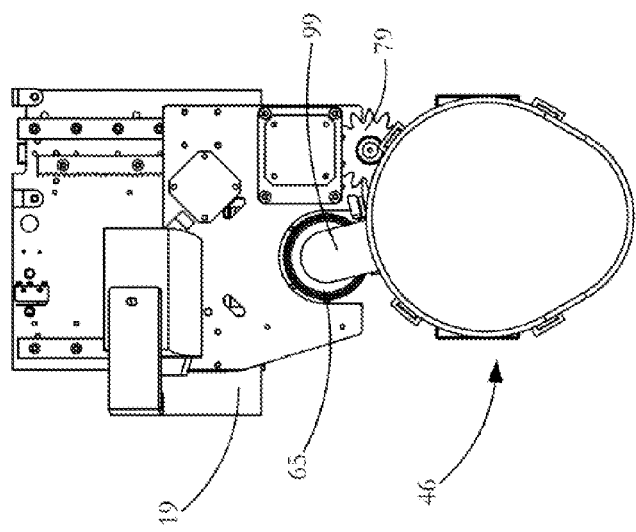
FIG. 15 is a plan view of the arrangement of FIG. 14.

In operation, a prescription is read and interpreted as previously described and instructions are sent to a control module indicating that a prescribed number of pills of a certain type are to be dispensed from an inventory store of such pills contained in a selected one of the pill dispensing modules 46. As a result of the instruction and as shown in FIG. 15, the platform 19 on which the drive gear 79 is mounted is moved on the carriages 21, 24 to a position adjacent the selected pill dispenser module. The drive gear is moved in the Z direction to mesh with the ring gear 78 of the selected module to spin the associated support tray 76. A first charge of pills that is already filling the chute 68 is drawn out of and away from the annular exit aperture 72 as the tray 76 spins. The size of the aperture 72 and the rate of spin of the tray 76 determine the rate at which pills are introduced to the singulating zone and moved from there to the pill exit zone.

Once the pills fall onto the tray upper surface, the ridges 82 and the wiper guide 84 interact so that the spinning tray drives the pills in a path governed by the shape of the wiper guide towards the boundary wall. The arcuate shape of the guide is such that the pills are first intercepted and then accelerated along the guide to encourage singulation as they are driven by the tray. Depending on the desired speed of dispensing, the tray can be driven at a range of possible spin rates to establish a corresponding range of pill dispensing rates. The driven pills tend to become distributed or singulated into a stream of separate pills by the time they reach the boundary wall 86.

The tray surface slopes downwardly and outwardly near the boundary wall to form an annular gutter region 80. As pills are singulated and reach the outer part of the tray, they fall into the gutter region and are further conveyed around the tray axis under the spin of the tray. Ideally, the singulated pills pass successively through an opening in the separator 88. If, however, multiple pills adhere together owing to static or other surface condition, the separator 88 allows passage of only one of the adhering pills at time with any adhering pill being stripped away.

In an alternative embodiment shown in FIGS. 11-13, the pill hopper which is shown in FIG. 11 with lid removed, is dished towards a central region where the limiter 70 is mounted. The hopper dish shape generally matches the form of the underlying tray which offers a very compact arrangement which is highly desirable for accommodation of the pill dispensing module in a dispensing kiosk where space is at a premium. An annular chute 68 has a series of ridges on its outer surface with a limiter 70 having sprung legs (not shown), each bearing a corresponding series of ridges to mesh with the chute ridges. In use, arms 45 of the limiter are manually grasped to raise or lower the limiter to bring a different pair of chute and limiter ridges into locking registration.

As shown in FIG. 12 which is illustrated with hopper layer removed, the module includes a tray 76 which is spun to singulate pills as in the previous embodiment. The arrangement includes a wiper guide 84 with a spring tab 94 mounted at its outer end. The spring tab and an adjacent part of a boundary wall 86 form a funnel region to receive pills as they are driven along by the spinning tray. The spring tab permits the passage of pills of various sizes without the requirement to tailor the dimensions of the funnel region. The spring tab also tends to split up pills arriving as an aggregated group. The spring tab is deforms elastically from its mounting orientation to avoid jamming of the funnel region by an aggregated group of pills that might occur with a rigid, unyielding member.

This embodiment also includes a deflector element 92 mounted on the boundary wall 86 to project into the path of pills being driven around a gutter region 80. Deflector elements of different sizes may be used depending on the particular size and shape of pills being dispensed. If a pill is oversize or is one of an aggregated group that have not been singulated by previously encountered parts of the module 46, the deflector element 92 acts to deflect the oversize pill or pills of the group, as applicable, away from the boundary wall 86 and back towards the hub part of the tray.

Pills nearing the exit zone are channelled into a lane 95 formed between the boundary wall 86 and an inner wall 97. At the end of the lane, the pills are driven off the edge of the tray by the tray's spin and through a gap in the boundary wall. The pills fall into the pill exit zone which is confined within a peripheral housing 99. The housing includes a gate 101 as shown in the scrap sectional view of FIG. 13. The gate is opened by actuation of a lever 103 which is normally spring biased to a closed position, but which is opened by an actuating element on the platform 19 in the course of a bottle being placed into the pill exit zone to receive falling pills.

Figure 18:
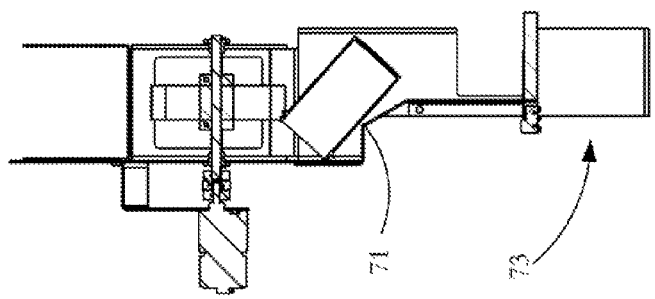
FIG. 18 is a sectional view from the front of the bottle delivery mechanism of FIG. 17.
Figure 17:
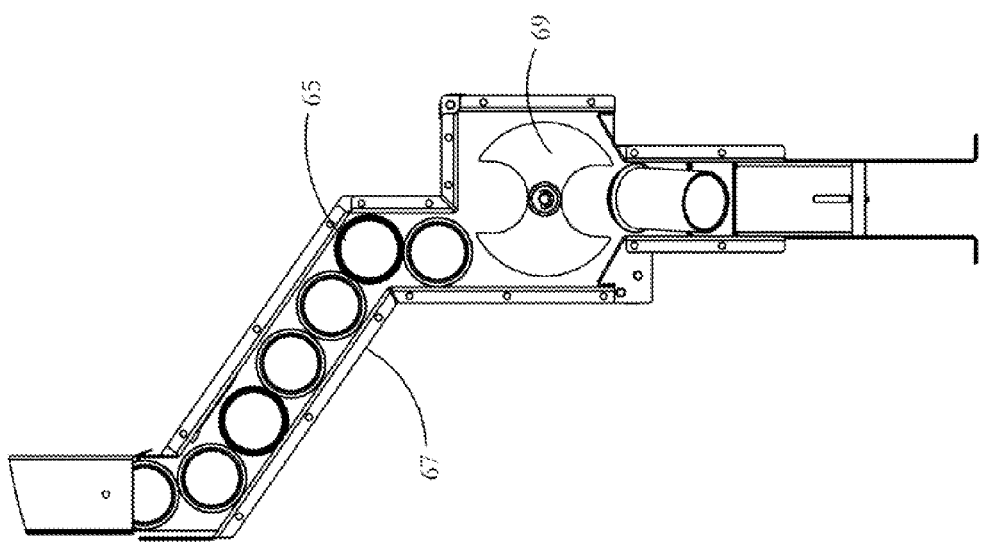
FIG. 17 is a sectional view from one side of part of a bottle delivery mechanism forming part of a pill dispensing module according to an embodiment of the invention.
Figure 20:
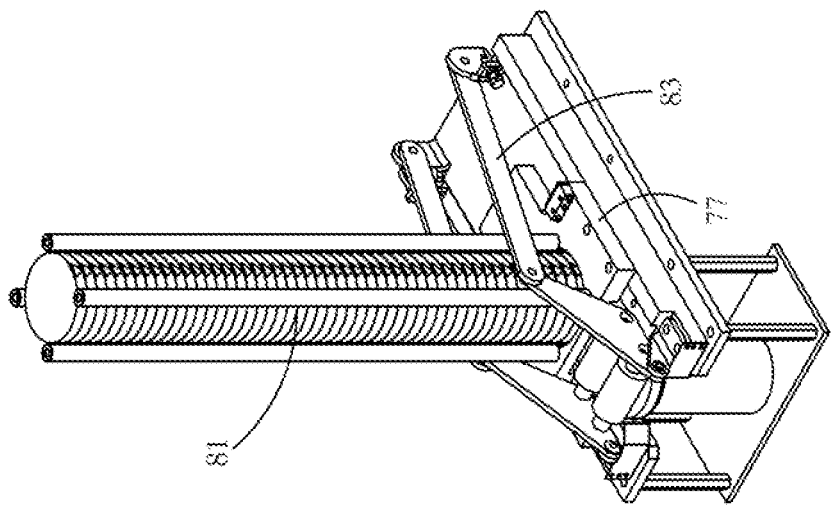
FIG. 20 is a perspective view of the bottle capping mechanism of FIG. 19.
Figure 19:
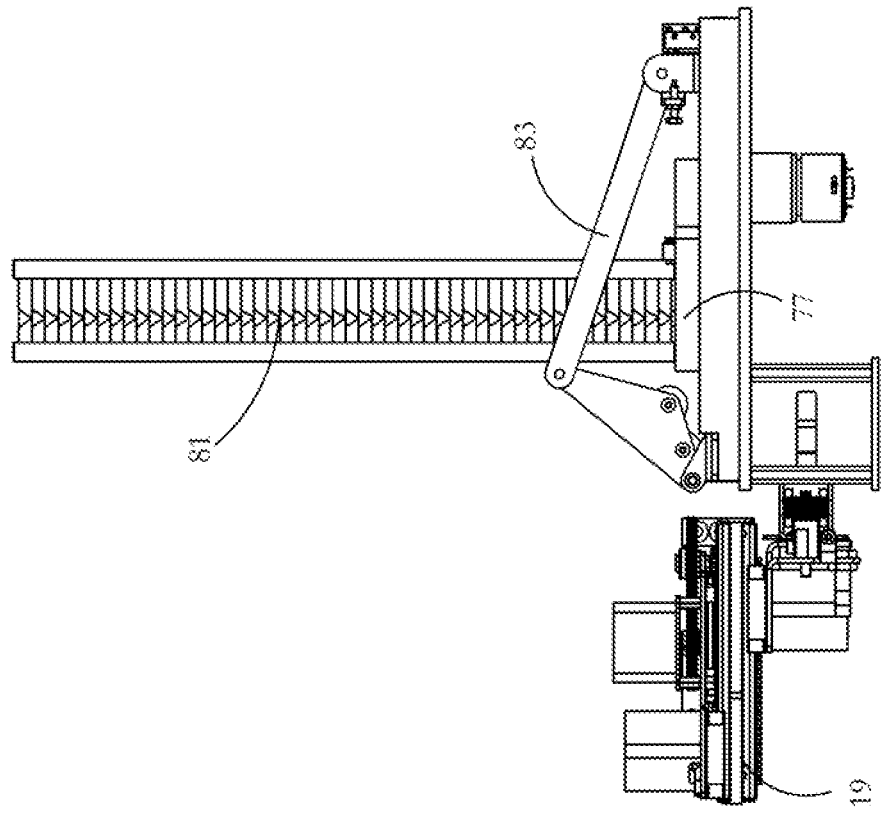
FIG. 19 is a side view of part of a bottle capping mechanism forming part of a pill dispensing module according to an embodiment of the invention.

Both the FIGS. 5-10 and the FIGS. 11-13 embodiments are operated in conjunction with a bottle supply sub-system shown in FIGS. 17 and 18 and a bottle capping sub-system shown in FIGS. 19 and 20. As shown in FIGS. 17 and 18, in the bottle supply sub-system, empty pill bottles 65 which are generally cylindrical in form are stored in a housing 67. When a pill dispensing operation is to take place, a transfer mechanism 69 is operated to allow the lowest of the stored bottles to drop from the store. The bottle is reorientated as it falls into a vertical orientation at a step formation 71 in the delivery path. The bottle is then held in an access zone 73 in preparation for being picked up and taken to the pill dispensing module by a gripper 75 mounted on the platform 19. The capping sub-system is charged with a stack of bottle caps. It includes a slider 77 which operates to slide the lowermost cap out of the stack to place the cap on top of an empty bottle 65 previously positioned at a capping zone by the gripper. A lever system 83 is then used to press the cap into position on the bottle.

Figure 16:
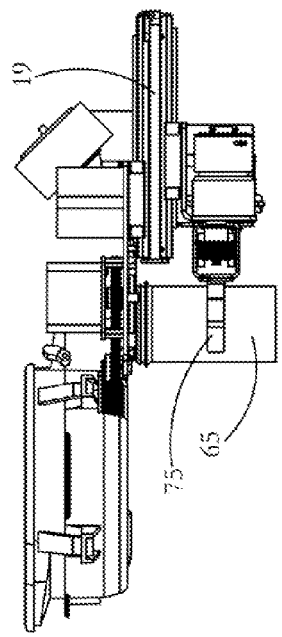
FIG. 16 is a side view of the arrangement of FIG. 14.

At appropriate stages of the pill dispensing process, the two sub-systems cooperate with or are actuated by operating mechanisms mounted on the platform 19 as shown in FIGS. 14-16. The actuating mechanisms include the gripper 75 which grips and moves the bottle from the access zone of the bottle supply sub-system. The gripper has opposed fingers that are brought towards one other to grip the bottle and moved apart to release it. Using the XY drive described previously and a rack and pinion mechanism to effect Z movement, the gripper is actuated to grip the empty bottle at the access zone of the bottle supply sub-system and to move it into the pill exit zone of the selected pill dispensing module as shown in FIG. 16. An optical emitter detector arrangement is used to detect the approach of the top of the bottle at which point, movement of the gripper is halted. When the bottle has been located and detected, the gate spring is released to open the gate 90. Pills are then delivered from the hopper, through the singulator, to the pill exit zone where they drop into the bottle. Pills that pass through the gate 90 fall past the optical emitter detector arrangement which operates to record a pill count as each pill drops into the pill bottle. When the number of pills counted matches the number of pills prescribed on the prescription, the gate 90 is closed.

The filled bottle is then taken by the gripper to the bottle capping sub-system of FIGS. 19 and 20. The sub-system is operated to place a cap over the filled bottle and, through the lever system, to apply downward pressure to the cap to snap press the cap into position to close and seal the bottle. Using the XY transport system previously described, the gripper takes the filled bottle to other stations such as a labeling station and then to a dispensing zone accessible to the kiosk user.

The figures illustrate preferred embodiments of pill dispenser for use in a networked arrangement to dispense both pre-packaged and bulk medicaments. The invention envisages other forms of dispenser for pills, lozenges and capsules and also envisages the dispensing and packaging of bulk liquid medicament in an arrangement that is similar to the pill dispensing module other than design changes to accommodate the handling of a liquid.

Both in the pill dispensing and the liquid dispensing arrangements, care is taken to avoid contamination of the medicament being dispensed. All locations where pills may be present are closed off from the surroundings and sealed against ingress of contaminants. In addition, where possible, dust, liquid and vapour seals are installed at locations where elements of the dispensing mechanism move relative to one another.

It will be appreciated that by using the pill dispensing modules described, a number of pills can be dispensed which need not conform to a "standard dosage" but can be tailored to the particular practice of the prescribing doctor or pharmacist. The modules also allow pills to be securely stored in bulk and in a sealed condition, to be touched only by dedicated handling equipment until dropped into a dispensary bottle or other package and dispensed to the user. The dispensing module has dimensions that allow it to be stored in a standard storage bay until required to be mounted at a kiosk, and is otherwise designed to enable reliable handling by automated handling equipment. It may also have security features to render the module tamper-resistant in transit.

Other variations and modifications of the invention will be apparent to those skilled in the art. The embodiments of the invention described and illustrated are not intended to be limiting. The principles of the invention contemplate many alternatives having advantages and properties evident in the exemplary embodiments.

The invention claimed is:

1. A pill dispenser comprising:
    a pill delivery station;
    a pill receiving station; and
    a pill singulator including:
        a tray for supporting pills delivered from the delivery station;
        a drive actuable to spin the tray about an axis to drive pills supported on the tray in a spin direction; and
        a guide to guide the driven pills towards the pill receiving station and to establish spacing between the driven pills, wherein:
        the pill delivery station includes:
            a pill hopper; and
            a delivery chute intermediate the hopper and the tray;
        a spacing between the chute and the tray permits metered delivery of pills from the chute on to the tray; and
        the chute is adjustable relative to the tray to alter the spacing.

2. The pill dispenser as defined in claim 1, wherein the drive is a driven gear forming part of a drive gear-driven gear combination, and the drive gear is mounted apart from the driven gear and movable into mesh with the driven gear to effect the spin of the tray.

3. The pill dispenser as defined in claim 1, wherein the spacing is such as to make rate of delivery of pills from the hopper through the chute to the tray dependent on a rate of spin of the tray.

4. The pill dispenser as defined in claim 1, wherein the guide is a wiper guide mounted close to a drive surface of the tray, the wiper guide shaped and positioned to guide pills delivered to a hub region and driven by the spinning tray away from the hub region.

5. The pill dispenser as defined in claim 4, wherein the tray is generally disc shaped, the wiper guide shaped and positioned to guide the driven pills from an axial region to a boundary region of the tray.

6. The pill dispenser as defined in claim 4, wherein the wiper guide has an arcuate form.

7. The pill dispenser as defined in claim 4, wherein the tray has a shallow conical profile.

8. The pill dispenser as defined in claim 4, wherein the drive surface has formations projecting therefrom to engage and drive the pills as the tray spins.

9. The pill dispenser as defined in claim 1, further comprising a boundary wall to confine the driven pills on the tray.

10. The pill dispenser as defined in claim 9, further comprising a restricting mechanism near the boundary wall to discourage further drive of the pills in the spin direction other than as singulated pills.

11. The pill dispenser as defined in claim 10, wherein the restricting mechanism including a spring member at an outer end of the wiper guide, thereby to accommodate passage of pills of various sizes.

12. The pill dispenser as defined in claim 11, wherein the restricting mechanism further including a projection extending from the boundary wall to intercept non-singulated combinations of pills and to deflect the intercepted pills away from the receiving station.

13. The pill dispenser as defined in claim 1, further comprising a lid to seal the pill hopper and pill singulator from above.

14. The pill dispenser as defined in claim 1, wherein:
    the drive is a driven gear forming part of a drive gear-driven gear combination, the drive gear mounted apart from the driven gear and movable into mesh with the driven gear to effect the spin of the tray;
    the pill delivery station includes:
        a pill hopper;
        a delivery chute intermediate the hopper and the tray; and
        a spacing between the chute and the tray:
            permitting metered delivery of pills from the chute on to the tray; and
            situated so as to make a rate of delivery of pills from the hopper through the chute to the tray dependent on a rate of spin of the tray;
    the chute is adjustable relative to the tray to alter the spacing;
    the guide is a wiper guide mounted close to a drive surface of the tray;
    the wiper guide shaped and positioned to guide pills delivered to a hub region and driven by the spinning tray away from the hub region;
    the drive surface has formations projecting therefrom to engage and drive the pills as the tray spins; and
    the pill dispenser further comprises:
        a deflecting mechanism to intercept driven pills after passing said restricting mechanism and to direct pills from the tray to a pill fall zone;
        a sensing mechanism to:

detect and count pills falling in the fall zone; and halt further dispensing of pills when a required number of pills have passed from the hopper to the fall zone; and a container positioning mechanism to transfer a container from a stored plurality thereof to the pill fall zone to receive pills falling in fall zone.

15. A pill dispenser comprising:
a pill delivery station;
a pill receiving station;
a pill singulator including:
   a tray for supporting pills delivered from the delivery station; and
   a drive actuable to spin the tray about an axis to drive pills supported on the tray in a spin direction;
   a guide to guide the driven pills towards the pill receiving station and to establish spacing between the driven pills;
and
a boundary wall to confine the driven pills on the tray; and
a restricting mechanism near the boundary wall to discourage further drive of the pills in the spin direction other than as singulated pills, wherein:
   the restricting mechanism further includes a projection extending from the boundary wall to:
     intercept non-singulated combinations of pills; and
     deflect the intercepted pills away from the receiving station;
   and
   the tray has a boundary region adjacent the boundary wall, the boundary region sloped downwardly towards the boundary wall to encourage driven pills to lodge against the boundary wall.

16. The pill dispenser as defined in claim 15, further comprising a deflecting mechanism to intercept driven pills after passing said restricting mechanism and to direct pills from the tray to a pill fall zone.

17. The pill dispenser as defined in claim 16, further comprising a sensing mechanism to detect and count pills falling in the fall zone and to halt further dispensing of pills when a required number of pills have passed from the hopper to the fall zone.

18. The pill dispenser as defined in claim 16, further comprising a container positioning mechanism to transfer a container from a stored plurality thereof to the pill fall zone to receive pills falling in fall zone.

19. A method of dispensing pills comprising:
delivering pills from a hopper to a singulating zone;
delivering pills:
   from the singulating zone to a receiving station; and
   at the singulating zone;
supporting the pills delivered from the hopper at a tray;
spinning the tray to drive the supported pills in a drive direction;
guiding the driven pills towards the pill receiving station;
establishing spacing between the driven, guided pills;
delivering pills from the hopper to the tray via a chute; and
setting a spacing between a part of the chute and a part of the tray to set a corresponding first delivery characteristic of pills delivered from the hopper to the tray.

20. A method of dispensing pills as claimed in claim 19, further comprises setting a spin rate of the tray to set a second delivery characteristic of pills delivered from the hopper to the tray.

21. A method of dispensing pills as claimed in claim 19, further comprising guiding the pills:
delivered to the tray from a region adjacent a spin axis of the tray to a region adjacent a boundary of the tray by guiding the driven pills along a guide extending from the axial region to the boundary region; and
in paths that are generally arcuate, whereby to singulate the pills.

* * * * *